United States Patent
Elizalde et al.

(10) Patent No.: US 8,580,887 B2
(45) Date of Patent: Nov. 12, 2013

(54) HIGH-FUNCTIONALITY POLYISOCYANATES CONTAINING URETHANE GROUPS

(75) Inventors: Oihana Elizalde, Charlotte, NC (US); Frederic Lucas, Ludwigshafen (DE); Angelika Maria Steinbrecher, Stuttgart (DE); Lydie Tuchbreiter, Charlotte, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/192,963

(22) Filed: Jul. 28, 2011

(65) Prior Publication Data

US 2012/0029144 A1    Feb. 2, 2012

Related U.S. Application Data

(60) Provisional application No. 61/369,078, filed on Jul. 30, 2010.

(51) Int. Cl.
  *C08L 75/00* (2006.01)
  *C07C 271/00* (2006.01)

(52) U.S. Cl.
  USPC .................... 524/589; 524/591; 560/157

(58) Field of Classification Search
  USPC ................... 524/189, 591, 589; 560/157
  See application file for complete search history.

(56) References Cited

U.S. PATENT DOCUMENTS

| | | | |
|---|---|---|---|
| 3,817,939 A | 6/1974 | Allen et al. | |
| 4,040,992 A | 8/1977 | Bechara et al. | |
| 4,324,879 A | 4/1982 | Bock et al. | |
| 4,596,678 A | 6/1986 | Merger et al. | |
| 4,596,679 A | 6/1986 | Hellbach et al. | |
| 4,847,346 A * | 7/1989 | Vorwerk et al. | 528/45 |
| 5,087,739 A | 2/1992 | Bohmholdt et al. | |
| 5,169,895 A * | 12/1992 | Coogan et al. | 524/591 |
| 5,502,147 A * | 3/1996 | Nodelman et al. | 528/49 |
| 6,228,472 B1 * | 5/2001 | Tazzia | 428/413 |
| 2012/0016074 A1 | 1/2012 | Elizalde et al. | |

FOREIGN PATENT DOCUMENTS

| | | |
|---|---|---|
| DE | 2 305 695 | 8/1973 |
| DE | 26 31 733 A1 | 2/1977 |
| DE | 28 06 731 A1 | 8/1979 |
| DE | 29 01 479 A1 | 7/1980 |
| DE | 38 06 276 A1 | 9/1989 |
| DE | 100 13 186 A1 | 9/2001 |
| DE | 100 13 187 A1 | 10/2001 |
| EP | 0 010 589 A1 | 5/1980 |
| EP | 0 126 299 A1 | 11/1984 |
| EP | 0 126 300 A1 | 11/1984 |
| EP | 0 355 443 A2 | 2/1990 |
| EP | 0 620 237 A2 | 10/1994 |
| EP | 1 061 091 A2 | 12/2000 |
| EP | 1 091 991 B1 | 4/2001 |
| EP | 1 497 351 B1 | 1/2005 |

OTHER PUBLICATIONS

New Low Viscous Polyisocyanates for VOC Compliant Systems, Mundstock et.al., Macromol. Symp., 2002. 187, 281, WILEY-VCH Verlag GmbH.*
U.S. Appl. No. 13/192,963, filed Jul. 28, 2011, Elizalde, et al.
U.S. Appl. No. 13/181,938, filed Jul. 13, 2011, Elizalde, et al.

* cited by examiner

*Primary Examiner* — Ling-siu Choi
*Assistant Examiner* — Aiqun Li
(74) *Attorney, Agent, or Firm* — Oblon, Spivak, McClelland, Maier & Neustadt, L.L.P.

(57) ABSTRACT

The present invention relates to new, urethane-group-containing polyisocyanates based on aliphatic and/or cycloaliphatic diisocyanates, and to their use.

11 Claims, No Drawings

HIGH-FUNCTIONALITY POLYISOCYANATES CONTAINING URETHANE GROUPS

The present invention relates to new, urethane-group-containing polyisocyanates based on aliphatic and/or cycloaliphatic diisocyanates, and to their use.

EP 1091991 B1 describes two-component polyurethane mixtures having a high-functionality, preferably at least tetrafunctional polyisocyanate as A component and a polyol as B component. The B component may also comprise low molecular weight diols to pentaols.

Polyisocyanate and polyol are used only in an NCO:OH ratio of 0.6 to 1.4:1, since the mixtures are coating compositions for coatings in which it is intended that substantially all of the reactive groups should have undergone reaction after curing.

EP 1497351 B1 describes the preparation of high-functionality polyisocyanates by trimerization of a mixture comprising aliphatic diisocyanates and uretdiones. Alcohols are not present.

EP 1061091 A describes at least difunctional polyisocyanates having allophanate groups by reaction of polyisocyanates with a monoalcohol and also, optionally, higher-functionality diols or polyols.

A disadvantage is that by means of an allophanate bonding it is not possible for more than two polyisocyanates to be linked with one another, and hence the functionality of the resultant products is limited.

EP 620237 A2 describes prepolymers formed from diisocyanates and polyols. Reaction with higher-functionality polyisocyanates is not disclosed.

A disadvantage of this is that the NCO functionality of the resultant products is not higher than the OH functionality of the polyols used.

DE-A 2305695 describes prepolymers formed from diisocyanates and low molecular weight polyols having 2 to 4 hydroxyl groups.

Reaction with higher-functionality polyisocyanates is not disclosed.

It was an object of the present invention to provide new polyisocyanates having a high functionality for coating materials, particularly for transparent varnishes and clearcoats, which have a high hardness and/or scratch resistance, more particularly even on curing at low temperatures and/or, in two-component polyurethane coating materials, exhibit accelerated drying and/or improved resistance to sulfuric acid.

This object is achieved by means of high-functionality polyisocyanates containing urethane groups and obtainable by
  reacting at least one tertiary di- or trialkanolamine (A), with
  at least one polyisocyanate (B), having a functionality of more than 2, which contains at least one isocyanurate, biuret, uretdione and/or allophanate group and is constructed from aliphatic and/or cycloaliphatic isocyanates,
  under reaction conditions under which urethane groups are formed between (A) and (B), with the proviso that
    the molar ratio of NCO groups to OH groups between (B) and (A) is at least 3:1.

The compound (A) may be a tertiary dialkanolamine or a trialkanolamine.

By a trialkanolamine is meant, in the context of this specification, the reaction product of ammonia with propylene oxide and/or ethylene oxide, preferably propylene oxide or ethylene oxide, more preferably ethylene oxide.

Preferred trialkanolamines (A) are those of the formula

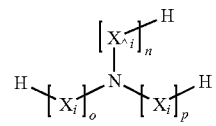

in which n, o, and p each independently of one another is an integer from 1 to 5, preferably 1 to 3, more preferably 1 to 2, and very preferably 1, and each $X_i$, for i=1 to n, 1 to o, and 1 to p, independently of one another, may be selected from the group consisting of —$CH_2$—$CH_2$—O—, —$CH_2$—$CH(CH_3)$—O—, and —CH($CH_3$)—$CH_2$—O—, and preferably —$CH_2$—$CH_2$—O—.

In one preferred embodiment the trialkanolamine (A) is 5-[bis(2'-hydroxyethyl)amino]-3-oxa-pentan-1-ol, triethanolamine or tripropanolamine, more preferably triethanolamine.

By a tertiary dialkanolamine is meant, in the context of this specification, the reaction product of a primary amine with propylene oxide and/or ethylene oxide, preferably propylene oxide or ethylene oxide, more preferably ethylene oxide.

Preferred tertiary dialkanolamines are

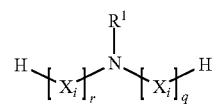

in which $R^1$ may be a straight-chain or branched $C_1$ to $C_{20}$ alkyl group, an optionally substituted $C_5$ to $C_{12}$ cycloalkyl group, an optionally substituted $C_7$ to $C_{10}$ aralkyl group, or an optionally substituted $C_6$-$C_{12}$ aryl group, q and r each independently of one another is an integer from 1 to 5, preferably 1 to 3, more preferably 1 to 2, and very preferably 1, and each $X_i$, for i=1 to q and 1 to r, independently of one another, may be selected from the group consisting of —$CH_2$—$CH_2$—O—, —$CH_2$—$CH(CH_3)$—O—, and —CH($CH_3$)—$CH_2$—O—, and preferably —$CH_2$—$CH_2$—O—.

In these definitions
a straight-chain or branched $C_1$ to $C_{20}$ alkyl group is for example methyl, ethyl, propyl, isopropyl, n-butyl, isobutyl, sec-butyl, tert-butyl, pentyl, hexyl, heptyl, octyl, 2-ethylhexyl, 2,4,4-trimethylpentyl, decyl, 1,1-dimethylpropyl, 1,1-dimethylbutyl or 1,1,3,3-tetramethylbutyl, an optionally substituted $C_5$ to $C_{12}$ cycloalkyl group is cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, and also a saturated or unsaturated bicyclic system such as norbornyl or norbornenyl, for example, an optionally substituted $C_7$ to $C_{10}$ aralkyl group is for example benzyl, 1-phenylethyl, 2-phenylethyl, α,α-dimethylbenzyl, benzhydryl, p-tolylmethyl, 1-(p-butylphenyl)-ethyl, o-, m- or p-chlorobenzyl, 2,4-dichlorobenzyl, o-, m- or p-methoxybenzyl or o-, m- or p-ethoxybenzyl, an optionally substituted $C_6$-$C_{12}$-aryl group is for example phenyl, 2-, 3- or 4-methylphenyl, α-naphthyl or β-naphthyl.

Among these radicals, $R^1$ is preferably a $C_5$ to $C_{12}$ cycloalkyl or $C_1$ to $C_{20}$ alkyl, more preferably $C_5$ to $C_6$ cycloalkyl or $C_1$ to $C_{10}$ alkyl, very preferably $C_1$ to $C_8$ alkyl, and more particularly $C_1$ to $C_4$ alkyl.

Preferred for $R^1$ are methyl, ethyl, n-propyl, isopropyl, n-butyl, sec-butyl, tert-butyl, pentyl, hexyl, heptyl, octyl, 2-ethylhexyl, phenyl, α- or β-naphthyl, benzyl, cyclopentyl or cyclohexyl.

Particularly preferred radicals $R^1$ are methyl, ethyl, n-propyl, isopropyl, n-butyl, tert-butyl, 2-ethylhexyl, cyclopentyl or cyclohexyl.

Especially preferred are methyl, ethyl, n-propyl, isopropyl, and n-butyl.

Examples of tertiary dialkanolamines are N-ethyldiethanolamine, N-methyldiethanolamine, N-butyldiethanolamine, N-cyclopentyldiethanolamine, N-cyclohexyldiethanolamine, N-ethyldipropanolamine, N-methyldipropanolamine, and N-butyldipropanolamine.

Preferred are N-ethyldiethanolamine, N-methyldiethanolamine, and N-butyldiethanolamine; particularly preferred are N-ethyldiethanolamine and N-methyldiethanolamine.

It is optionally possible to use at least one diol (A1) and/or polyol (A2) in addition to the compound (A), in amounts, for example, such that up to 70% of the total amount of hydroxyl groups employed come from the diol (A1) and/or polyol (A2), for example, 10% to 70%, preferably 15% to 55%, and more preferably 20% to 40%.

Polyols (A2) have a functionality of at least 3, for example, 3 to 6, preferably 3 to 4, more preferably 3 or 4, and very preferably 3.

Examples of polyols (A2) are trimethylolbutane, trimethylolpropane, trimethylolethane, pentaerythritol, glycerol, ditrimethylolpropane, dipentaerythritol, sorbitol, mannitol, diglycerol, threitol, erythritol, adonitol (ribitol), arabitol (lyxitol), xylitol, dulcitol (galactitol), maltitol, and isomalt.

Preferred polyols are those having a functionality of between 3 and 4, more preferably those having a functionality of 3.

Preferred polyols are trimethylolpropane, trimethylolethane, pentaerythritol, glycerol, ditrimethylolpropane, and dipentaerythritol, more preferably trimethylolpropane, pentaerythritol, and glycerol, and very preferably trimethylolpropane and glycerol.

Examples of diols (A1) are aliphatic diols which have two to 20, preferably 2 to 12, carbon atoms, more preferably 1,2-ethanediol, 2,2-dimethyl-1,2-ethanediol, 1,2-propanediol, 1,3-propanediol, 2,2-dimethyl-1,3-propanediol, 2-methyl-1,3-propanediol, 2-ethyl-1,3-propane-diol, 2-ethyl-2-methyl-1,3-propanediol, 2-butyl-2-ethyl-1,3-propanediol, 1,2-butanediol, 1,3-butanediol, 1,4-butanediol, 3-methylpentane-1,5-diol, 1,6-hexanediol, 2-ethyl-1,3-hexane-diol, 2-propyl-1,3-heptanediol, 1,8-octanediol, 2,4-diethyloctane-1,3-diol, 1,10-decanediol, or cycloaliphatic diols which have six to 20 carbon atoms, preferably bis(4-hydroxycyclohexane)-isopropylidene, tetramethylcyclobutanediol, 1,2-, 1,3- or 1,4-cyclohexanediol, cyclooctanediol, norbornanediol, 2,2-bis(4-hydroxycyclohexyl)propane, and 1,1-, 1,2-, 1,3-, and 1,4-cyclohexane-dimethanol.

Among these the aliphatic diols are preferred, preferably 1,2-ethanediol, 1,2-propanediol, 1,3-propanediol, 2,2-dimethyl-1,3-propanediol, 1,4-butanediol, 1,6-hexanediol, 2-ethyl-1,3-hexanediol and 2-propyl-1,3-heptanediol, more preferably 2,2-dimethyl-1,3-propanediol, 1,4-butanediol, 1,6-hexanediol, 2-ethyl-1,3-hexanediol and 2-propyl-1,3-heptanediol, and very preferably 1,4-butanediol and 1,6-hexanediol.

In one preferred embodiment of the present invention the polyol (A2) is used in alkoxylated form.

By an alkoxylated polyol in this context is meant a polyol which is reacted formally on at least one hydroxyl group with one or more identical or different alkylene oxides.

Examples of suitable alkylene oxides for such alkoxylation are ethylene oxide, propylene oxide, n-butylene oxide, isobutylene oxide, vinyloxirane and/or styrene oxide.

The alkylene oxide chain may be composed preferably of ethylene oxide, propylene oxide and/or butylene oxide units. A chain of this kind may be composed of one species of one alkylene oxide, or of a mixture of alkylene oxides. Where a mixture is used, the different alkylene oxide units may be present statistically or as a block or blocks of individual species. Preferred alkylene oxide is ethylene oxide, propylene oxide or a mixture thereof, more preferably either ethylene oxide or propylene oxide, and very preferably ethylene oxide.

The number of alkylene oxide units in the chain is, for example, 1 to 10, preferably 1 to 5, more preferably 1-4, and more particularly 1-3, based on the respective hydroxyl groups of the polyol.

Particularly preferred are alkoxylated polyols of the formulae (IIa) to (IIc),

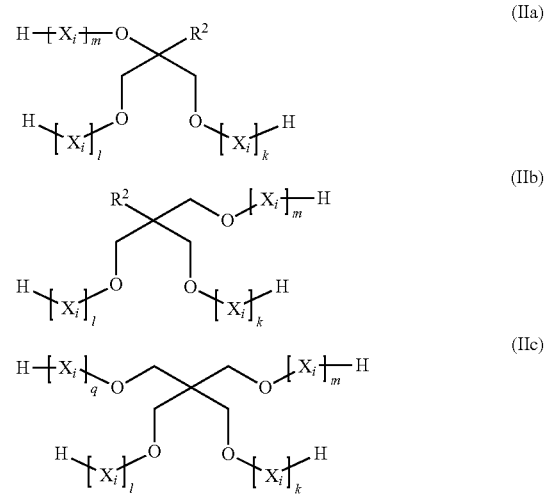

in which $R^2$ is hydrogen or $C_1$-$C_{18}$ alkyl, k, l, m, and q, independently of one another, are each an integer from 1 to 10, preferably 1 to 5, more preferably 1 to 4, and very preferably 1 to 3, and each $X_i$ for i=1 to k, 1 to l, 1 to m, and 1 to q, independently of one another, may be selected from the group consisting of —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O—, and —CHPh-$CH_2$—O—, preferably from the group of —$CH_2$—$CH_2$—O—, —$CH_2$—$CH(CH_3)$—O—, and —$CH(CH_3)$—$CH_2$—O—, and more preferably —$CH_2$—$CH_2$—O—, in which Ph is phenyl and Vin is vinyl.

The compounds in question are preferably pentaerythritol, trimethylolethane, trimethylolpropane or glycerol which per hydroxyl group is singly to pentuply, more preferably singly to quadruply, and very preferably singly to triply ethoxylated, propoxylated or mixedly ethoxylated and propoxylated, and more particularly exclusively ethoxylated, or, especially, unalkoxylated.

The ratio of diols (A1) to polyols (A2) is preferably from 10:90 to 90:10 (based on the molar amounts of diol and polyol), more preferably from 20:80 to 80:20, very preferably from 30:70 to 70:30, and more particularly from 40:60 to 60:40.

The polyisocyanate (B) has a functionality of more than 2, preferably at least 2.2, more preferably at least 2.4, very preferably at least 2.8, and more particularly at least 3.

The polyisocyanates (B) are constructed from aliphatic and/or cycloaliphatic, preferably either aliphatic or cycloaliphatic, diisocyanates.

The diisocyanates are preferably isocyanates having 4 to 20 C atoms. Examples of customary diisocyanates are aliphatic diisocyanates such as tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, trimethylhexane diisocyanate or tetramethyihexane diisocyanate, cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane or 2,4- or 2,6-diisocyanato-1-methylcyclohexane, and also 3 (or 4),8 (or 9)-bis(isocyanatomethyl)tricyclo[$5.2.1.0^{2,6}$]decane isomer mixtures.

Preferred diisocyanates are 1,6-hexamethylene diisocyanate, isophorone diisocyanate and/or 4,4'- or 2,4'-di(isocyanatocyclohexyl)methane, more preferably 1,6-hexamethylene diisocyanate and/or isophorone diisocyanate and very preferably 1,6-hexamethylene diisocyanate.

Mixtures of the stated diisocyanates may also be present.

Polyisocyanates contemplated include polyisocyanates containing isocyanurate groups, uretdione diisocyanates, polyisocyanates containing biuret groups, and polyisocyanates containing urethane and/or allophanate groups, formed from linear or branched $C_4$-$C_{20}$ alkylene diisocyanates or cycloaliphatic diisocyanates having a total of 6 to 20 C atoms, or mixtures thereof.

The polyisocyanates which can be used preferably have an isocyanate group (calculated as NCO, molecular weight=42 g/mol) content of 10% to 60% by weight, based on the diisocyanate and polyisocyanate (mixture), preferably 12% to 50% by weight, and more preferably 12% to 40% by weight.

Particular preference is given to hexamethylene diisocyanate, 1,3-bis(isocyanatomethyl)cyclohexane, isophorone diisocyanate, and di(isocyanatocyclohexyl)methane or their polyisocyanates, very preferably isophorone diisocyanate and hexamethylene diisocyanate or their polyisocyanates, and with more particular preference hexamethylene diisocyanate or its polyisocyanates.

Preference extends to
1) Polyisocyanates containing isocyanurate groups and formed from aliphatic and/or cycloaliphatic diisocyanates. Particular preference here is given to the corresponding aliphatic and/or cycloaliphatic isocyanatoisocyanurates, and more particularly to those based on hexamethylene diisocyanate and/or isophorone diisocyanate. The isocyanurates present are more particularly trisisocyanatoalkyl and/or trisisocyanatocycloalkyl isocyanurates, which represent cyclic trimers of the diisocyanates, or mixtures with their higher homologs containing more than one isocyanurate ring. The isocyanatoisocyanurates generally have an NCO content of 10% to 30% by weight, more particularly 15% to 25% by weight, and an average NCO functionality of 2.6 to 4.5.
2) Uretdione diisocyanates having aliphatically and/or cycloaliphatically attached isocyanate groups, and more particularly those derived from hexamethylene diisocyanate or isophorone diisocyanate. Uretdione diisocyanates are cyclic dimerization products of diisocyanates.
   The uretdione diisocyanates can be used as polyisocyanates (B) in a mixture with other polyisocyanates, more particularly those specified under 1).
3) Polyisocyanates containing biuret groups and having cycloaliphatically or aliphatically attached isocyanate groups, more particularly tris(6-isocyanatohexyl)biuret or its mixtures with its higher homologs. These polyisocyanates containing biuret groups generally have an NCO content of 18% to 22% by weight and an average NCO functionality of 2.8 to 4.5.
4) Polyisocyanates containing urethane and/or allophanate groups and having aliphatically or cycloaliphatically attached isocyanate groups, of the kind obtainable, for example, by reaction of excess amounts of hexamethylene diisocyanate or of isophorone diisocyanate with monohydric or polyhydric alcohols such as, for example, methanol, ethanol, isopropanol, n-propanol, n-butanol, isobutanol, sec-butanol, tert-butanol, n-hexanol, n-heptanol, n-octanol, n-decanol, n-dodecanol (lauryl alcohol), 2-ethylhexanol, n-pentanol, stearyl alcohol, cetyl alcohol, lauryl alcohol, ethylene glycol monomethyl ether, ethylene glycol monoethyl ether, 1,3-propanediol monomethyl ether, cyclopentanol, cyclohexanol, cyclooctanol, cyclododecanol, or mixtures thereof. These polyisocyanates containing urethane and/or allophanate groups generally have an NCO content of 12% to 20% by weight and an average NCO functionality of 2.5 to 4.5.

The polyisocyanates can be used in a mixture, including where appropriate a mixture with diisocyanates.

For the preparation of the high-functionality, urethane-group-containing polyisocyanates, polyisocyanate (B) and compound (A) are reacted with one another, with or without solvent, under urethanization conditions.

"Urethanization conditions" here mean that the reaction conditions are selected such that reaction of the isocyanate-group-containing component (B) and the hydroxyl-group-containing component (A) results at least partly in urethane groups being formed.

The temperature for this reaction is generally up to 150° C., preferably up to 120° C., more preferably below 100° C., and very preferably below 90° C., and the reaction is usually carried out in the presence of at least one catalyst that catalyzes the urethanization reaction. The reaction can alternatively be carried out in the absence of a catalyst.

Generally speaking, the temperature of the reaction ought to be at least 20° C., preferably at least 30° C., more preferably at least 40° C., and very preferably at least 50° C.

Catalysts in this context are those compounds whose presence in a reactants mixture produces a higher fraction of urethane-group-containing reaction products than does the same reactants mixture in the absence of such compounds under the same reaction conditions.

Examples of these compounds are organic amines, more particularly tertiary aliphatic, cycloaliphatic or aromatic amines, and/or Lewis-acidic organometallic compounds.

Examples of suitable Lewis-acidic organometallic compounds include tin compounds, such as tin(II) salts of organic carboxylic acids, e.g., tin(II) diacetate, tin(II) dioctoate, tin (II) bis(ethylhexanoate), and tin(II) dilaurate, and the dialkyltin(IV) salts of organic carboxylic acids, e.g., dimethyltin diacetate, dibutyltin diacetate, dibutyltin dibutyrate, dibutyltin bis(2-ethylhexanoate), dibutyltin dilaurate, dibutyltin maleate, dioctyltin dilaurate, and dioctyltin diacetate. Zinc (II) salts as well may be used, such as zinc(II) dioctoate, for example. Also possible are metal complexes such as acetylacetonates of iron, of titanium, of aluminum, of zirconium, of manganese, of nickel, of zinc, and of cobalt. Other metal catalysts are described by Blank et al. in Progress in Organic Coatings, 1999, vol. 35, pages 19-29.

Preferred Lewis-acidic organometallic compounds are dimethyltin diacetate, dibutyltin dibutyrate, dibutyltin bis(2-ethylhexanoate), dibutyltin dilaurate, dioctyltin dilaurate, zinc(II) dioctoate, zirconium acetylacetonate, and zirconium 2,2,6,6-tetramethyl-3,5-heptanedionate.

Additionally, bismuth catalysts and cobalt catalysts, and also cesium salts, can be among the catalysts employed. Cesium salts contemplated include those compounds in which the following anions are used: $F^-$, $Cl^-$, $ClO^-$, $ClO_3^-$, $ClO_4^-$, $Br^-$, $I^-$, $IO_3^-$, $CN^-$, $OCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, $(OC_nH_{2n+1})^-$, $(C_nH_{2n-1}O_2)^-$, $(C_nH_{2n-3}O_2)^-$, and $(C_{n+1}H_{2n-2}O_4)^{2-}$, where n stands for the numbers 1 to 20.

Preferred in this context are cesium carboxylates in which the anion conforms to the formulae $(C_nH_{2n-1}O_2)^-$ and $(C_{n+1}H_{2n-2}O_4)^{2-}$, with n being 1 to 20. Particularly preferred cesium salts have monocarboxylate anions of the general formula $(C_nH_{2n-1}O_2)^-$, where n stands for the numbers 1 to 20. Particularly noteworthy in this context are formate, acetate, propionate, hexanoate, and 2-ethylhexanoate.

As catalysts it is possible, furthermore, to employ the following:

organometallic salts of the formula $(A)_n$—R—O—CO—$O^\ominus M^\oplus$ as per U.S. Pat. No. 3,817,939, in which:
A is a hydroxyl group or a hydrogen atom,
n is a number from 1 to 3,
R is a polyfunctional linear or branched, aliphatic or aromatic hydrocarbon radical, and
$M^\oplus$ is a cation, such as an alkali metal cation or a quaternary ammonium cation, such as tetraalkylammonium, and also
quaternary hydroxyalkylammonium compounds of the formula

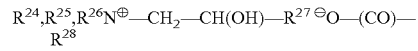

as catalyst as per DE-A-26 31 733 (U.S. Pat. No. 4,040,992), with the definitions stated therein for the radicals.

Particularly suitable as catalysts for the process are quaternary ammonium salts corresponding to the formula

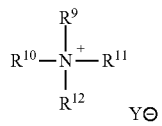

with
$Y^\ominus$=carboxylate ($R^{13}COO^-$), fluoride ($F^-$), carbonate ($R^{13}O(CO)O^-$) or hydroxide ($OH^-$), of the kind described for $Y^-=OH^-$ in U.S. Pat. No. 4,324,879 and in German Laid-Open Specifications 2,806,731 and 2,901,479.

The radical $Y^\ominus$ is preferably a carboxylate, carbonate or hydroxide and more preferably a carboxylate or hydroxide.

$R^{13}$ therein is hydrogen, $C_1$ to $C_{20}$ alkyl, $C_6$ to $C_{12}$ aryl or $C_7$ to $C_{20}$ arylalkyl, each of which may optionally be substituted. Preferably $R^{13}$ is hydrogen or $C_1$ to $C_8$ alkyl.

Preferred quaternary ammonium salts are those in which the radicals $R^9$ to $R^{12}$ are identical or different alkyl groups having 1 to 20, preferably 1 to 4, carbon atoms, which are unsubstituted or substituted by hydroxyl or phenyl groups.

Two of the radicals $R^9$ to $R^{12}$ may also form, together with the nitrogen atom and possibly with a further nitrogen or oxygen atom, a heterocyclic five-, six- or seven-membered ring. In each case the radicals $R^9$ to $R^{11}$ may also be ethylene radicals which form, together with the quaternary nitrogen atom and a further tertiary nitrogen atom, a bicyclic triethylenediamine structure, provided that the radical $R^{12}$ in that case is a hydroxyalkyl group having 2 to 4 carbon atoms in which the hydroxyl group is located preferably in the 2-position relative to the quaternary nitrogen atom. The hydroxy-substituted radical or radicals may also comprise other substituents, examples being $C_1$ to $C_4$ alkyloxy substituents.

The ammonium ions in this context may also be part of a mono- or multi-membered ring system, derived for example from piperazine, morpholine, piperidine, pyrrolidine, quinuclidine or diazabicyclo[2.2.2]octane.

Examples of groups $R^9$ to $R^{12}$ containing 1 to 20 carbon atoms are, independently of one another, methyl, ethyl, propyl, isopropyl, n-butyl, sec-butyl, tert-butyl, pentyl, hexyl, heptyl, octyl, 2-ethylhexyl, 2,4,4-trimethylpentyl, nonyl, isononyl, decyl, dodecyl, tetradecyl, hexadecyl, octa-decyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, chloromethyl, 2-chloroethyl, trichloromethyl, trifluoromethyl, 1,1-dimethyl-2-chloroethyl, 2-methoxyisopropyl, 2-ethoxyethyl, 2-hydroxyethyl, 2-hydroxypropyl, 3-hydroxypropyl, 4-hydroxybutyl, 6-hydroxyhexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl, 6-ethoxyhexyl, phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, methylnaphthyl, isopropylnaphthyl, chloronaphthyl, 2,6-dimethylphenyl, 2,4,6-trimethylphenyl, 2,6-dimethoxyphenyl, 2,6-dichlorophenyl, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, chlorocyclohexyl, dichlorocyclohexyl, dichlorocyclopentyl, norbornyl or norbornenyl.

The radicals $R^9$ to $R^{12}$ are preferably, independently of one another, $C_1$ to $C_4$ alkyl. $R^{12}$ may additionally be benzyl or a radical of the formula

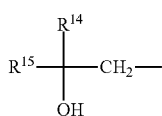

in which $R^{14}$ and $R^{15}$ independently of one another may be hydrogen or $C_1$ to $C_4$ alkyl.

Particularly preferred radicals $R^9$ to $R^{12}$ are, independently of one another, methyl, ethyl, and n-butyl, and for $R^{12}$ additionally benzyl, 2-hydroxyethyl, and 2-hydroxypropyl.

For the process of the invention it is possible with preference to use the following catalysts:

quaternary ammonium hydroxides, preferably N,N,N-trimethyl-N-benzylammonium hydroxide and N,N,N-trimethyl-N-(2-hydroxypropyl)ammonium hydroxide, as per DE-A-38 06 276.

Hydroxyalkyl-substituted quaternary ammonium hydroxides as per EP-A-10 589 (U.S. Pat. No. 4,324,879).

Organometallic salts of the formula $(A)_n$—R—O—CO—$O^{\ominus}M^{\oplus}$ as per U.S. Pat. No. 3,817,939, in which A is a hydroxyl group or a hydrogen atom, n is a number from 1 to 3, R is a polyfunctional linear or branched, aliphatic or aromatic hydrocarbon radical, and M is a cation of a strong base, e.g., an alkali metal cation or a quaternary ammonium cation, such as tetraalkylammonium.

Preferred catalysts are zinc(II) salts, and of these particularly zinc acetylacetonate.

Additionally preferred is dibutyltin dilaurate.

Depending on its activity, the catalyst is used normally in amounts of 0.001 to 10 mol % based on isocyanate groups employed, preferably 0.5 to 8, more preferably 1 to 7, and very preferably 2 to 5 mol %.

The polyisocyanate (B) is used in an at least threefold excess of the NCO groups, based on the hydroxyl groups in the compound (A), preferably in an at least 4-fold excess, more preferably in an at least 5-fold excess, and very preferably in an at least 6-fold excess.

The unreacted portion of polyisocyanate (B) may either be separated off or, preferably, remain in the reaction mixture.

The reaction is carried out preferably without solvent, but may also be carried out in the presence of at least one solvent. Similarly, the reaction mixture obtained may be formulated in a solvent after the end of the reaction.

Solvents which can be used are those which do not have groups that are reactive toward isocyanate groups, and in which the polyisocyanates are soluble to an extent of at least 10%, preferably at least 25%, more preferably at least 50%, very preferably at least 75%, more particularly at least 90%, and especially at least 95% by weight.

Examples of solvents of this kind are aromatic hydrocarbons (including alkylated benzenes and naphthalenes) and/or (cyclo)aliphatic hydrocarbons, and mixtures thereof, chlorinated hydrocarbons, ketones, esters, alkoxylated alkanoic acid alkyl esters, ethers, or mixtures of the solvents.

Preferred aromatic hydrocarbon mixtures are those which comprise predominantly aromatic $C_7$ to $C_{14}$ hydrocarbons and may span a boiling range from 110 to 300° C., particular preference being given to toluene, o-, m- or p-xylene, trimethylbenzene isomers, tetramethylbenzene isomers, ethylbenzene, cumene, tetrahydronaphthalene, and mixtures comprising these.

Examples thereof are the Solvesso® grades from Exxon-Mobil Chemical, especially Solvesso® 100 (CAS no. 64742-95-6, predominantly $C_9$ and $C_{10}$ aromatics, boiling range about 154-178° C.), 150 (boiling range about 182-207° C.), and 200 (CAS no. 64742-94-5), and also the Shellsol® grades from Shell, Caromax® (e.g., Caromax® 18) from Petrochem Carless, and Hydrosol from DHC (e.g., as Hydrosol® A 170). Hydrocarbon mixtures comprising paraffins, cycloparaffins, and aromatics are also available commercially under the designations Kristalloel (examples being Kristalloel 30, boiling range about 158-198° C., or Kristalloel 60: CAS no. 64742-82-1), white spirit (for example, likewise CAS no. 64742-82-1) or solvent naphtha (light: boiling range about 155-180° C., heavy: boiling range about 225-300° C.). The aromatics content of hydrocarbon mixtures of this kind is generally more than 90%, preferably more than 95%, more preferably more than 98%, and very preferably more than 99% by weight. It may make sense to use hydrocarbon mixtures having a particularly reduced naphthalene content.

Examples of (cyclo)aliphatic hydrocarbons include decalin, alkylated decalin, and isomer mixtures of linear or branched alkanes and/or cycloalkanes. The aliphatic hydrocarbons content is generally less than 5%, preferably less than 2.5%, and more preferably less than 1% by weight.

Examples of esters include n-butyl acetate, ethyl acetate, 1-methoxyprop-2-yl acetate, and 2-methoxyethyl acetate.

Examples of ethers are tetrahydrofuran (THF), dioxane, and the dimethyl, diethyl or di-n-butyl ethers of ethylene glycol, diethylene glycol, triethylene glycol, propylene glycol, dipropylene glycol or tripropylene glycol.

Examples of ketones are acetone, diethyl ketone, ethyl methyl ketone, isobutyl methyl ketone, methyl amyl ketone, and tert-butyl methyl ketone.

In one preferred embodiment of the present invention the high-functionality polyisocyanates of the invention are formulated with a solvent. A preferred solvent is n-butyl acetate.

The concentration of the polyisocyanate of the invention in the solution ought to be at least 50%, preferably at least 60%, and more preferably at least 70% by weight.

The high-functionality polyisocyanates of the invention, containing urethane groups, generally have an NCO functionality of more than 2, preferably at least 3, more preferably at least 4, very preferably at least 5, and more particularly more than 6.

The high-functionality polyisocyanates of the invention, containing urethane groups, generally have a number-average molecular weight Mn of 1000 to 20 000, preferably of 1200 to 10 000, and more preferably of 1500 to 5000 g/mol and a weight-average molecular weight Mw of 1000 to 50 000 and preferably of 1500 to 30 000. The molecular weights can be determined by gel permeation chromatography with a suitable polymer standard and tetrahydrofuran or dimethylformamide as eluent.

The high-functionality, urethane-group-containing polyisocyanates of the invention find application for example in two-component polyurethane coating materials featuring at least one component comprising at least two isocyanate-reactive groups (binder). For this purpose the high-functionality, urethane-group-containing polyisocyanates of the invention may be used alone or in a mixture with other polyisocyanates (C) as a crosslinker component.

Such other polyisocyanates (C) are obtainable by oligomerization of monomeric isocyanates.

The monomeric isocyanates used for this may be aromatic, aliphatic or cycloaliphatic, preferably aliphatic or cycloaliphatic, which is referred to for short in this text as (cyclo)aliphatic; aliphatic isocyanates are particularly preferred.

Aromatic isocyanates are those which comprise at least one aromatic ring system, in other words not only purely aromatic compounds but also araliphatic compounds.

Cycloaliphatic isocyanates are those which comprise at least one cycloaliphatic ring system.

Aliphatic isocyanates are those which comprise exclusively linear or branched chains, i.e., acyclic compounds.

The monomeric isocyanates are preferably diisocyanates, which carry precisely two isocyanate groups. They can, however, in principle also be monoisocyanates, having one isocyanate group.

In principle, higher isocyanates having on average more than 2 isocyanate groups are also contemplated. Suitability therefor is possessed for example by triisocyanates such as triisocyanatononane, 2,4,6-triisocyanatotoluene, triphenylmethane triisocyanate or 2,4,4'-triisocyanatodiphenyl ether, or the mixtures of diisocyanates, triisocyanates, and higher polyisocyanates that are obtained, for example, by phosgenation of corresponding aniline/formaldehyde condensates and represent methylene-bridged polyphenyl polyisocyanates.

These monomeric isocyanates do not contain any substantial products of reaction of the isocyanate groups with themselves.

The monomeric isocyanates are preferably isocyanates having 4 to 20 C atoms. Examples of typical diisocyanates are aliphatic diisocyanates such as tetramethylene diisocyanate, pentamethylene 1,5-diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, trimethylhexane diisocyanate or tetramethylhexane diisocyanate, cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis-(isocyanatomethyl)cyclohexane or 2,4-, or 2,6-diisocyanato-1-methylcyclohexane, and also 3 (or 4), 8 (or 9)-bis(isocyanatomethyl)tricyclo[5.2.1.0$^{2,6}$]decane isomer mixtures, and also aromatic diisocyanates such as tolylene 2,4- or 2,6-diisocyanate and the isomer mixtures thereof, m- or p-xylylene diisocyanate, 2,4'- or 4,4'-diisocyanatodiphenylmethane and the isomer mixtures thereof, phenylene 1,3- or 1,4-diisocyanate, 1-chlorophenylene 2,4-diisocyanate, naphthylene 1,5-diisocyanate, diphenylene 4,4'-diisocyanate, 4,4'-diisocyanato-3,3'-dimethylbiphenyl, 3-methyldiphenylmethane 4,4'-diisocyanate, tetramethylxylylene diisocyanate, 1,4-diisocyanatobenzene or diphenyl ether 4,4'-diisocyanate.

Particular preference is given to hexamethylene 1,6-diisocyanate, 1,3-bis(isocyanatomethyl)cyclohexane, isophorone diisocyanate, and 4,4'- or 2,4'-di(isocyanatocyclohexyl)methane, very particular preference to isophorone diisocyanate and hexamethylene 1,6-diisocyanate, and especial preference to hexamethylene 1,6-diisocyanate.

Mixtures of said isocyanates may also be present.

Isophorone diisocyanate is usually in the form of a mixture, specifically a mixture of the cis and trans isomers, generally in a proportion of about 60:40 to 80:20 (w/w), preferably in a proportion of about 70:30 to 75:25, and more preferably in a proportion of approximately 75:25.

Dicyclohexylmethane 4,4'-diisocyanate may likewise be in the form of a mixture of the different cis and trans isomers.

It is possible to use not only those diisocyanates obtained by phosgenating the corresponding amines but also those prepared without the use of phosgene, i.e., by phosgene-free processes. According to EP-A-0 126 299 (U.S. Pat. No. 4,596,678), EP-A-126 300 (U.S. Pat. No. 4,596,679), and EP-A-355 443 (U.S. Pat. No. 5,087,739), for example, (cyclo)aliphatic diisocyanates, such as hexamethylene 1,6-diisocyanate (HDI), isomeric aliphatic diisocyanates having 6 carbon atoms in the alkylene radical, 4,4'- or 2,4'-di(isocyanatocyclohexyl)methane, and 1-isocyanato-3-isocyanatomethyl-3,5,5-trimethylcyclohexane (isophorone diisocyanate or IPDI) can be prepared by reacting the (cyclo)aliphatic diamines with, for example, urea and alcohols to give (cyclo)aliphatic biscarbamic esters and subjecting said esters to thermal cleavage into the corresponding diisocyanates and alcohols. The synthesis takes place usually continuously in a circulation process and in the presence, if desired, of N-unsubstituted carbamic esters, dialkyl carbonates, and other by-products recycled from the reaction process. Diisocyanates obtained in this way generally contain a very low or even unmeasurable fraction of chlorinated compounds, which is advantageous, for example, in applications in the electronics industry.

In one embodiment the isocyanates used have a total hydrolyzable chlorine content of less than 200 ppm, preferably of less than 120 ppm, more preferably less than 80 ppm, very preferably less than 50 ppm, in particular less than 15 ppm, and especially less than 10 ppm. This can be measured by means, for example, of ASTM specification D4663-98. Of course, though, monomeric isocyanates having a higher chlorine content can also be used, of up to 500 ppm, for example.

It will be appreciated that it is also possible to employ mixtures of those monomeric isocyanates which have been obtained by reacting the (cyclo)aliphatic diamines with, for example, urea and alcohols and cleaving the resulting (cyclo)aliphatic biscarbamic esters, with those diisocyanates which have been obtained by phosgenating the corresponding amines.

The polyisocyanates (C) which can be formed by oligomerizing the monomeric isocyanates are generally characterized as follows:

The average NCO functionality of such compounds is in general at least 1.8 and can be up to 8, preferably 2 to 5, and more preferably 2.4 to 4.

The isocyanate group content after oligomerization, calculated as NCO=42 g/mol, is generally from 5% to 25% by weight unless otherwise specified.

The polyisocyanates (C) are preferably compounds as follows:

1) Polyisocyanates containing isocyanurate groups and derived from aromatic, aliphatic and/or cycloaliphatic diisocyanates. Particular preference is given in this context to the corresponding aliphatic and/or cycloaliphatic isocyanatoisocyanurates and in particular to those based on hexamethylene diisocyanate and isophorone diisocyanate. The isocyanurates present are, in particular, trisisocyanatoalkyl and/or trisisocyanatocycloalkyl isocyanurates, which constitute cyclic trimers of the diisocyanates, or are mixtures with their higher homologs containing more than one isocyanurate ring. The isocyanatoisocyanurates generally have an NCO content of 10% to 30% by weight, in particular 15% to 25% by weight, and an average NCO functionality of 2.6 to 8.

2) Polyisocyanates containing uretdione groups and having aromatically, aliphatically and/or cycloaliphatically attached isocyanate groups, preferably aliphatically and/or cycloaliphatically attached, and in particular those derived from hexamethylene diisocyanate or isophorone diisocyanate. Uretdione diisocyanates are cyclic dimerization products of diisocyanates. The polyisocyanates containing uretdione groups are obtained in the context of this invention as a mixture with other polyisocyanates, more particularly those specified under 1). For this purpose the diisocyanates can be reacted under reaction conditions under which not only uretdione groups but also the other polyisocyanates are formed, or the uretdione groups are formed first of all and are subsequently reacted to give the other polyisocyanates, or the diisocyanates are first reacted to give the other polyisocyanates, which are subsequently reacted to give products containing uretdione groups.

3) Polyisocyanates containing biuret groups and having aromatically, cycloaliphatically or aliphatically attached, preferably cycloaliphatically or aliphatically attached, isocyanate groups, especially tris(6-isocyanatohexyl)biuret or its mixtures with its higher homologs. These polyisocyanates containing biuret groups generally have an NCO content of 18% to 22% by weight and an average NCO functionality of 2.8 to 6.

4) Polyisocyanates containing urethane and/or allophanate groups and having aromatically, aliphatically or cycloaliphatically attached, preferably aliphatically or cycloaliphatically attached, isocyanate groups, such as may be obtained, for example, by reacting excess amounts of diisocyanate, such as of hexamethylene diisocyanate or of isophorone diisocyanate, with mono- or polyhydric alcohols. These polyisocyanates containing urethane and/or allophanate groups generally have an NCO content of 12% to 24% by weight and an average NCO functionality of 2.5 to 4.5. Polyisocyanates of this kind containing urethane and/or allophanate groups may be prepared without catalyst or, preferably, in the presence of catalysts, such as ammonium carboxylates or ammonium hydroxides, for example, or allophanatization catalysts, such as Zn(II) compounds, for example, in each case in the presence of monohydric, dihydric or polyhydric, preferably monohydric, alcohols.

5) Polyisocyanates comprising oxadiazinetrione groups, derived preferably from hexamethylene diisocyanate or isophorone diisocyanate. Polyisocyanates of this kind comprising oxadiazinetrione groups are accessible from diisocyanate and carbon dioxide.

6) Polyisocyanates comprising iminooxadiazinedione groups, derived preferably from hexamethylene diisocyanate or isophorone diisocyanate. Polyisocyanates of this kind comprising iminooxadiazinedione groups are preparable from diisocyanates by means of specific catalysts.

7) Uretonimine-modified polyisocyanates.

8) Carbodiimide-modified polyisocyanates.

9) Hyperbranched polyisocyanates, of the kind known for example from DE-A1 10013186 or DE-A1 10013187.

10) Polyurethane-polyisocyanate prepolymers, from di- and/or polyisocyanates with alcohols.

11) Polyurea-polyisocyanate prepolymers.

12) The polyisocyanates 1)-11), preferably 1), 3), 4), and 6), can be converted, following their preparation, into polyisocyanates containing biuret groups or urethane/allophanate groups and having aromatically, cycloaliphatically or aliphatically attached, preferably (cyclo)aliphatically attached, isocyanate groups. The formation of biuret groups, for example, is accomplished by addition of water or by reaction with amines. The formation of urethane and/or allophanate groups is accomplished by reaction with monohydric, dihydric or polyhydric, preferably monohydric, alcohols, in the presence if desired of suitable catalysts. These polyisocyanates containing biuret or urethane/allophanate groups generally have an NCO content of 18% to 22% by weight and an average NCO functionality of 2.8 to 6.

13) Hydrophilically modified polyisocyanates, i.e., polyisocyanates which as well as the groups described under 1-12 also comprise groups which result formally from addition of molecules containing NCO-reactive groups and hydrophilizing groups to the isocyanate groups of the above molecules. The latter groups are nonionic groups such as alkylpolyethylene oxide and/or ionic groups derived from phosphoric acid, phosphonic acid, sulfuric acid or sulfonic acid, and/or their salts.

14) Modified polyisocyanates for dual cure applications, i.e., polyisocyanates which as well as the groups described under 1-12 also comprise groups resulting formally from addition of molecules containing NCO-reactive groups and UV-crosslinkable or actinic-radiation-crosslinkable groups to the isocyanate groups of the above molecules. These molecules are, for example, hydroxyalkyl (meth) acrylates and other hydroxyvinyl compounds.

The diisocyanates or polyisocyanates recited above may also be present at least partly in blocked form.

Classes of compounds used for blocking are described in D. A. Wicks, Z. W. Wicks, Progress in Organic Coatings, 36, 148-172 (1999), 41, 1-83 (2001) and also 43, 131-140 (2001).

Examples of classes of compounds used for blocking are phenols, imidazoles, triazoles, pyrazoles, oximes, N-hydroxyimides, hydroxybenzoic esters, secondary amines, lactams, CH-acidic cyclic ketones, malonic esters or alkyl acetoacetates.

In one preferred embodiment of the present invention the polyisocyanate (C) is selected from the group consisting of isocyanurates, biurets, urethanes, and allophanates, preferably from the group consisting of isocyanurates, urethanes, and allophanates, more preferably from the group consisting of isocyanurates and allophanates; in particular it is a polyisocyanate containing isocyanurate groups.

In one particularly preferred embodiment the polyisocyanate (C) encompasses polyisocyanates comprising isocyanurate groups and obtained from 1,6-hexamethylene diisocyanate.

In one further particularly preferred embodiment the polyisocyanate encompasses a mixture of polyisocyanates comprising isocyanurate groups and obtained from 1,6-hexamethylene diisocyanate and from isophorone diisocyanate.

In one particularly preferred embodiment the polyisocyanate (C) is a mixture comprising low-viscosity polyisocyanates, preferably polyisocyanates comprising isocyanurate groups, having a viscosity of 600-1500 mPa*s, more particularly below 1200 mPa*s, low-viscosity urethanes and/or allophanates having a viscosity of 200-1600 mPa*s, more particularly 600-1500 mPa*s, and/or polyisocyanates comprising iminooxadiazinedione groups.

In this specification, unless noted otherwise, the viscosity is reported at 23° C. in accordance with DIN EN ISO 3219/A.3 in a cone/plate system with a shear rate of $1000\ s^{-1}$.

The high-functionality, urethane-group-containing polyisocyanates of the invention may if desired be used in a mixture with other polyisocyanates (C), as crosslinker components, with at least one binder in polyurethane coating materials.

Generally speaking, for polyisocyanate compositions, in other words the sum of the compounds containing isocyanate groups, 50% to 100% by weight of the high-functionality, urethane-group-containing polyisocyanates of the invention are used, preferably 50% to 90% by weight, and more preferably 60% to 80% by weight, and 0% to 50% by weight of other polyisocyanates (C), preferably 10% to 50%, more preferably 20% to 40% by weight, with the proviso that the sum is always 100% by weight.

The binders may be, for example, polyacrylate polyols, polyester polyols, polyether polyols, polyurethane polyols; polyurea polyols; polyester-polyacrylate polyols; polyesterpolyurethane polyols; polyurethane-polyacrylate polyols, polyurethane-modified alkyd resins; fatty-acid-modified polyester-polyurethane polyols, copolymers with allyl ethers, graft polymers of the stated groups of compounds having, for example, different glass transition temperatures, and also mixtures of the stated binders. Preference is given to polyacrylate polyols, polyester polyols, and polyether polyols.

Preferred OH numbers, measured in accordance with DIN 53240-2, are 40-350 mg KOH/g resin solids for polyesters, preferably 80-180 mg KOH/g resin solids, and 15-250 mg KOH/g resin solids for polyacrylateols, preferably 80-160 mg KOH/g.

Additionally the binders may have an acid number in accordance with DIN EN ISO 3682 of up to 200 mg KOH/g, preferably up to 150 and more preferably up to 100 mg KOH/g.

Polyacrylate polyols preferably have a molecular weight $M_n$ of at least 1000, more preferably at least 2000, and very preferably at least 5000 g/mol. The molecular weight $M_n$ may in principle have no upper limit, and may preferably be up to 200 000, more preferably up to 100 000, very preferably up to 80 000, and more particularly up to 50 000 g/mol.

The latter may be, for example, monoesters of α,β-unsaturated carboxylic acids, such as acrylic acid, methacrylic acid (identified for short in this specification as "(meth)acrylic acid"), with diols or polyols which have preferably 2 to 20 C atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,4-butanediol, 1,5-pentanediol, neopentyl glycol, neopentyl glycol hydroxypivalate, 2-ethyl-1,3-propanediol, 2-methyl-1,3-propanediol, 2-butyl-2-ethyl-1,3-propanediol, 1,6-hexanediol, 2-methyl-1,5-pentanediol, 2-ethyl-1,4-butanediol, 2-ethyl-1,3-hexanediol, 2,4-diethyloctane-1,3-diol, 2,2-bis(4-hydroxycyclohexyl)propane, 1,1-, 1,2-, 1,3-and 1,4-bis(hydroxymethyl)cyclohexane, 1,2-, 1,3- or 1,4-cyclohexanediol, glycerol, trimethylolethane, trimethylolpropane, trimethylolbutane, pentaerythritol, ditrimethylolpropane, dipentaerythritol, sorbitol, mannitol, diglycerol, threitol, erythritol, adonitol (ribitol), arabitol (lyxitol), xylitol, dulcitol (galactitol), maltitol, isomalt, polyTHF with a molar weight between 162 and 4500, preferably 250 to 2000, poly-1,3-propanediol or polypropylene glycol with a molar weight between 134 and 2000, or polyethylene glycol with a molar weight between 238 and 2000.

Preference is given to 2-hydroxyethyl acrylate, 2-hydroxyethyl methacrylate, 2- or 3-hydroxypropyl acrylate, 1,4-butanediol monoacrylate or 3-(acryloyloxy)-2-hydroxypropyl acrylate, and particular preference to 2-hydroxyethyl acrylate and/or 2-hydroxyethyl methacrylate.

The hydroxyl-bearing monomers are used in the copolymerization in a mixture with other polymerizable monomers, preferably free-radically polymerizable monomers, preferably those composed to an extent of more than 50% by weight of $C_1$-$C_{20}$, preferably $C_1$ to $C_4$ alkyl (meth)acrylate, (meth) acrylic acid, vinylaromatics having up to 20 C atoms, vinyl esters of carboxylic acids comprising up to 20 C atoms, vinyl halides, nonaromatic hydrocarbons having 4 to 8 C atoms and 1 or 2 double bonds, unsaturated nitriles, and mixtures thereof. Particular preference is given to the polymers composed to an extent of more than 60% by weight of $C_1$-$C_{10}$ alkyl (meth)acrylates, styrene and its derivatives, vinylimidazole or mixtures thereof.

In addition the polymers may contain hydroxy-functional monomers corresponding to the above hydroxyl group content and, if desired, further monomers, examples being (meth) acrylic acid glycidyl epoxy esters, ethylenically unsaturated acids, more particularly carboxylic acids, acid anhydrides or acid amides.

Further polymers are, for example, polyesterols, as are obtainable by condensing polycarboxylic acids, especially dicarboxylic acids, with polyols, especially diols. In order to ensure a polyester polyol functionality that is appropriate for the polymerization, use is also made in part of triols, tetrols, etc, and also triacids etc.

Polyester polyols are known for example from Ullmanns Encyklopadie der technischen Chemie, 4th edition, volume 19, pp. 62 to 65. It is preferred to use polyester polyols which are obtained by reacting dihydric alcohols with dibasic carboxylic acids. In lieu of the free polycarboxylic acids it is also possible to use the corresponding polycarboxylic anhydrides or corresponding polycarboxylic esters of lower alcohols or mixtures thereof to prepare the polyester polyols. The polycarboxylic acids may be aliphatic, cycloaliphatic, aromatic or heterocyclic and may if desired be substituted, by halogen atoms for example, and/or unsaturated. Examples thereof that may be mentioned include the following:

Oxalic acid, maleic acid, fumaric acid, succinic acid, glutaric acid, adipic acid, sebacic acid, dodecanedioic acid, o-phthalic acid, isophthalic acid, terephthalic acid, trimellitic acid, azelaic acid, 1,4-cyclohexanedicarboxylic acid or tetrahydrophthalic acid, suberic acid, azelaic acid, phthalic anhydride, tetrahydrophthalic anhydride, hexahydrophthalic anhydride, tetrachlorophthalic anhydride, endomethylenetetrahydrophthalic anhydride, glutaric anhydride, maleic anhydride, dimeric fatty acids, their isomers and hydrogenation products, and also esterifiable derivatives, such as anhydrides or dialkyl esters, $C_1$-$C_4$ alkyl esters for example, preferably methyl, ethyl or n-butyl esters, of the stated acids are employed. Preference is given to dicarboxylic acids of the general formula HOOC—$(CH_2)_y$—COON, where y is a number from 1 to 20, preferably an even number from 2 to 20, and more preferably succinic acid, adipic acid, sebacic acid, and dodecanedicarboxylic acid.

Suitable polyhydric alcohols for preparing the polyesterols include 1,2-propanediol, ethylene glycol, 2,2-dimethyl-1,2-ethanediol, 1,3-propanediol, 1,2-butanediol, 1,3-butanediol, 1,4-butane-diol, 3-methylpentane-1,5-diol, 2-ethylhexane-1,3-diol, 2,4-diethyloctane-1,3-diol, 1,6-hexane-diol, polyTHF having a molar mass of between 162 and 4500, preferably 250 to 2000, poly-1,3-propanediol having a molar mass between 134 and 1178, poly-1,2-propanediol having a molar mass between 134 and 898, polyethylene glycol having a molar mass between 106 and 458, neopentyl glycol, neopentyl glycol hydroxypivalate, 2-ethyl-1,3-propanediol, 2-methyl-1,3-propanediol, 2,2-bis(4-hydroxycyclohexyl)propane, 1,1-, 1,2-, 1,3- and 1,4-cyclohexane-dimethanol, 1,2-, 1,3- or 1,4-cyclohexanediol, trimethylolbutane, trimethylolpropane, trimethylolethane, neopentyl glycol, pentaerythritol, glycerol, ditrimethylolpropane, dipentaerythritol, sorbitol, mannitol, diglycerol, threitol, erythritol, adonitol (ribitol), arabitol (lyxitol), xylitol, dulcitol (galactitol), maltitol or isomalt, which if desired may have been alkoxylated as described above.

Preferred alcohols are those of the general formula HO—$(CH_2)_x$—OH, where x is a number from 1 to 20, preferably an even number from 2 to 20. Preferred are ethylene glycol, butane-1,4-diol, hexane-1,6-diol, octane-1,8-diol and dodecane-1,12-diol. Additionally preferred is neopentyl glycol.

Also suitable, furthermore, are polycarbonate diols of the kind obtainable, for example, by reacting phosgene with an excess of the low molecular mass alcohols specified as synthesis components for the polyester polyols.

Also suitable are lactone-based polyester diols, which are homopolymers or copolymers of lactones, preferably hydroxy-terminated adducts of lactones with suitable difunctional starter molecules. Suitable lactones are preferably those which derive from compounds of the general formula HO—$(CH_2)_z$—COOH, where z is a number from 1 to 20 and where one H atom of a methylene unit may also have been substituted by a $C_1$ to $C_4$ alkyl radical. Examples are ε-caprolactone, β-propiolactone, gamma-butyrolactone and/or methyl-ε-caprolactone, 4-hydroxybenzoic acid, 6-hydroxy-2-naphthoic acid or pivalolactone, and mixtures thereof. Examples of suitable starter components include the low molecular mass dihydric alcohols specified above as a synthesis component for the polyester polyols. The corresponding polymers of ε-caprolactone are particularly preferred. Lower polyester diols or polyether diols as well can be used as starters for preparing the lactone polymers. In lieu of the polymers of lactones it is also possible to use the corresponding, chemically equivalent polycondensates of the hydroxycarboxylic acids corresponding to the lactones.

Also suitable as polymers, furthermore, are polyetherols, which are prepared by addition reaction of ethylene oxide, propylene oxide or butylene oxide with H-active components. Polycondensates of butanediol are also suitable.

In addition it is possible to use hydroxy-functional carboxylic acids, such as dimethylolpropionic acid or dimethylolbutanoic acid, for example.

The polymers can of course also be compounds containing primary or secondary amino groups.

For the purpose of preparing the polyurethane coating materials, polyisocyanate composition and binder are mixed with one another in a molar ratio of isocyanate groups to isocyanate-reactive groups of 0.1:1 to 10:1, preferably 0.2:1 to 5:1, more preferably 0.3:1 to 3:1, very preferably 0.5:1 to 2:1, more particularly 0.8:1 to 1.2:1, and especially 0.9:1 to 1.1:1, it being possible if desired to mix in further, typical coatings constituents, and the resulting mixture is applied to the substrate.

Subsequently the coating-material mixture is cured under suitable conditions. Depending on application, this may take place, for example, at 100 to 140° C., in the case for example of coating materials in OEM applications, or in a lower temperature range of 20 to 80° C., for example.

Depending on temperature, this usually takes not more than 12 hours, preferably up to 8 hours, more preferably up to 6, very preferably up to 4, and in particular up to 3 hours.

It is additionally possible for coating compositions to comprise 0% to 10% by weight of at least one UV stabilizer.

Suitable stabilizers comprise typical UV absorbers such as oxanilides, triazines, and benzotriazole (the latter available as Tinuvin® grades from Ciba-Spezialitätenchemie), and benzophenones.

They may further comprise 0% to 5% by weight of suitable free-radical scavengers, examples being sterically hindered amines such as 2,2,6,6-tetramethylpiperidine, 2,6-di-tert-butylpiperidine or derivatives thereof, e.g., bis(2,2,6,6-tetramethyl-4-piperidyl) sebacate.

Furthermore, coating compositions may further comprise 0% to 10% by weight of further, typical coatings additives.

Further, typical coatings additives that can be used include, for example, antioxidants, activators (accelerants), fillers, pigments, dyes, antistatic agents, flame retardants, thickeners, thixotropic agents, surface-active agents, viscosity modifiers, plasticizers or chelating agents.

Suitable thickeners, in addition to free-radically (co)polymerized (co)polymers, include typical organic and inorganic thickeners such as hydroxymethylcellulose or bentonite.

Chelating agents which can be used include, for example, ethylenediamineacetic acid and salts thereof, and also β-diketones.

Suitable fillers comprise silicates, examples being silicates obtainable by hydrolysis of silicon tetrachloride, such as Aerosil® from Degussa, siliceous earth, talc, aluminum silicates, magnesium silicates, calcium carbonates, etc.

The substrates are coated by typical methods known to the skilled worker, with at least one coating composition being applied in the desired thickness to the substrate to be coated, and any volatile constituents of the coating composition being removed, if appropriate with heating. This operation may if desired be repeated one or more times. Application to the substrate may take place in a known way, as for example by spraying, troweling, knifecoating, brushing, rolling, rollercoating, flowcoating, laminating, injection backmolding or coextruding.

The thickness of a film of this kind for curing may be from 0.1 µm up to several mm, preferably from 1 to 2000 µm, more preferably 5 to 200 µm, very preferably from 5 to 60 µm (based on the coating material in the state in which the solvent has been removed from the coating material).

Additionally provided by the present invention are substrates coated with a coating material comprising the urethane-group-containing polyisocyanates of the invention.

Polyurethane coating materials of this kind are especially suitable for applications requiring particularly high application reliability, exterior weathering resistance, optical qualities, solvent resistance, chemical resistance, and water resistance.

The two-component coating compositions and coating formulations obtained are in principle suitable for coating substrates such as wood, wood veneer, paper, cardboard, paperboard, textile, film, leather, nonwoven, plastics surfaces, glass, ceramic, mineral building materials, such as molded cement blocks and fiber-cement slabs, or metals, which in each case may optionally have been precoated or pretreated. With particular preference, however, they are suitable for the coating of plastics surfaces and metallic substrates.

These coating compositions are used preferably as clearcoat, basecoat, and topcoat(s), primers and surfacers, and in particular they are suitable, on account of their high scratch resistance, as topcoat material, preferably as clearcoat material, more particularly in coatings on (large) vehicles and aircraft, and in automobile finishes as OEM and refinish.

It is an advantage of the urethane-group-containing polyisocyanates of the invention that in clearcoats they produce high scratch resistance in conjunction with good elasticity. Moreover, the products of the invention usually result in a relatively low viscosity.

EXAMPLES

Polyisocyanate A:
Basonat® HI 100 from BASF SE, HDI isocyanurate having an NCO content of 22.2% and a viscosity of 3500 mPa*s at 23° C., functionality of about 3.4.

Hazen Color Number:
Method for determining the yellowing of technical liquids to DIN ISO 6271. An acidic solution of potassium hexachloroplatinate is used as the standard.

Comparative Example 1

Basonat® HI 100 from BASF SE: HDI isocyanurate having an NCO content of 22.2% and a viscosity of 2800 mPa*s at 23° C.

Comparative Example 2

Desmodur® N3790 from Bayer AG: HDI isocyanurate (90% in butyl acetate), having an NCO content of 17.8% and a viscosity of 2150 mPa*s at 23° C.

Example 1

300.00 g (0.524 mol) of polyisocyanate A and 13.00 g (0.087 mol) of triethanolamine were mixed in 134.1 g of butyl acetate. The solution was two-phase at room temperature and had an NCO content of 15.0%. The solution became homogeneous after the temperature was raised from room temperature to 60° C. The mixture was reacted with addition of dibutyltin dilaurate catalyst. After 1 hour at 60° C., the NCO content was 12.1%. The batch was then cooled and filtered through Seitz T5500 filters. The corresponding product had a viscosity of 440 mPas at 23° C. and a color number of 21 Hazen.

Example 2

360.99 g (0.630 mol) of polyisocyanate A and 10.43 g (0.070 mol) of triethanolamine were mixed in 159.2 g of butyl acetate. The solution was two-phase at room temperature and had an NCO content of 14.5%. The solution became homogeneous after the temperature was raised from room temperature to 60° C. The mixture was reacted with addition of dibutyltin dilaurate catalyst. After 1.5 hours at 60° C., the NCO content was 12.2%. The batch was then cooled and filtered through Seitz T5500 filters. The corresponding product had a viscosity of 320 mPas at 23° C. and a color number of 23 Hazen.

Example 3

343.80 g (0.600 mol) of polyisocyanate A and 7.45 g (0.050 mol) of triethanolamine were mixed in 150.54 g of butyl acetate. The solution was two-phase at room temperature and had an NCO content of 15.5%. The solution became homogeneous after the temperature was raised from room temperature to 60° C. The mixture was reacted with addition of dibutyltin dilaurate catalyst. After 3 hours at 60° C., the NCO content was 13.5%. The batch was then cooled and filtered through Seitz T5500 filters. The corresponding product had a viscosity of 120 mPas at 23° C. and a color number of 21 Hazen.

Example 4

343.80 g (0.600 mol) of polyisocyanate A were mixed into 153.5 g of butyl acetate, and 5.40 g of 1,4-butanediol (0.060 mol) and 8.94 g (0.060 mol) of triethanolamine were added. The solution was hazy at room temperature and had an NCO content of 14.8%. The solution became transparent when the temperature was raised from room temperature to 60° C. The mixture was reacted with addition of dibutyltin dilaurate catalyst. After 2.5 hours at 60° C. the NCO content was 11.8%. The batch was then cooled and filtered through Seitz T5500 filters. The corresponding product had a viscosity of 370 mPas at 23° C. and a color number of 28 Hazen.

Performance Testing:

The inventive and comparative polyisocyanates were mixed with acrylic-acid-free, hydroxy-functional polyacrylate polyols (Joncryl® 922, BASF; solids content=80% in butyl acetate; OH number=143 mg KOH/g, corresponding to a stoichiometric NCO/OH ratio of 1:1) and were adjusted with butyl acetate to an application viscosity of 20 s (DIN 53 211, cup 4 mm efflux nozzle). Using a drawing frame, coatings with a wet film thickness of 200 µm were applied to metal panels. The resultant clearcoats were flashed off at room temperature for 10 minutes and, for determining the scratch resistance and acid resistance, were cured at 60° C. over a period of 30 minutes. Prior to the tests the coating films were stored for 24 h at 23±2° C. and 50±10% humidity.

Test Methods:

The gel time is considered to be the time between coating-material formulation and complete gelling of the coating material.

For determining the drying rate of the coating-material surface, the coating material, after application, was contacted at regular intervals with a cotton pad. The test is ended when cotton fibers no longer adhere to the coating-material surface.

The pendulum hardness was determined by the method of König (EN ISO 1522).

The cross-cut was determined in accordance with EN ISO 2409. The ratings in that test are between 0 (very good adhesive strength) and 5 (very poor adhesive strength).

For determining the scratch resistance of the coating material, the surface is subjected to scratching using a scouring pad containing corundum particles, under a weight of 500 g. The damage is determined via the gloss value of the coating material. The reflow is determined by heating, at the temperature indicated in the table and for the time indicated in the table, after scratching via 50 double rubs.

The sulfuric acid resistance was tested (etch test) in accordance with EN ISO 2812-1 (method 3) in the temperature range of 35-75° C.:

Using a pipette, a 25 µm drop of 1% strength sulfuric acid was applied to a coating material, cured at a predetermined temperature (30 minutes at 80 or 130° C.) on a gradient oven panel, and this metal panel was heated in the gradient oven at 35-75° C. for 30 minutes. The panel was subsequently washed with water and dried. The parameter reported is the lowest temperature at which initial etching on the coating material is discernible.

The temperature of the curing of the coating material is identified in the table by 80° C. or 130° C.

n.d. stands for measurement values not determined.

|  | Comp. example 1 | Comp. example 2 | Example 1 |
|---|---|---|---|
| Cotton test (min) | 260 | 210 | 75 |
| Etch 80° C.; 1% sulfuric acid, 0 h [° C.] | <30 | <30 | 32 |
| Testing after 24 h | <30 | <30 | 32 |
| Appearance of the coating material film | clear | clear | clear |
| Scratch resistance 80° C.; 20° [%] | 94 | 93 | 95 |
| Scratch resistance 80° C.; 60° [%] | 100 | 100 | 100 |
| 10 double rubs; 20° [%] | 2 | 8 | 33 |
| 10 double rubs; 60° [%] | 7 | 21 | 51 |
| 50 double rubs; 20° [%] | 1 | 1 | 3 |
| 50 double rubs; 60° [%] | 5 | 6 | 9 |
| Pendulum damping 80° C. | 38 | 49 | 74 |
| Pendulum damping 130° C. | 62 | 73 | 113 |
|  | Example | Example | Example |

-continued

|  | 2 | 3 | 4 |
|---|---|---|---|
| Cotton test (min) | 100 | 175 | 80 |
| Etch 80° C.; 1% sulfuric acid, 0 h [° C.] | 38 | 39 | 37 |
| Testing after 24 h | 39 | 38 | 40 |
| Appearance of the coating material film | clear | clear | clear |
| Scratch resistance 80° C.; 20° [%] | 94 | 94 | 94 |
| Scratch resistance 80° C.; 60° [%] | 99 | 99 | 99 |
| 10 double rubs; 20° [%] | 12 | 15 | 26 |
| 10 double rubs; 60° [%] | 30 | 29 | 40 |
| 50 double rubs; 20° [%] | 2 | 1 | 2 |
| 50 double rubs; 60° [%] | 7 | 5 | 6 |
| Pendulum damping 80° C. | 74 | 65 | 75 |
| Pendulum damping 130° C. | 105 | 102 | 115 |

The invention claimed is:

1. A high-functionality polyisocyanate comprising urethane groups and obtainable by
   reacting at least one tertiary di- or trialkanolamine (A), with
   at least one polyisocyanate (B), having a functionality of more than 2, under reaction conditions under which urethane groups are formed between (A) and (B), with the proviso that
   the molar ratio of NCO groups to OH groups between (B) and (A) is at least 4:1 and said high-functionality polyisocyanate has an NCO content of at least 11.8 by weight and wherein the polyisocyanate (B) comprises polyisocyanates which comprise isocyanurate groups, are based on 1,6-hexamethylene diisocyanate, and have a viscosity of 600-3000 mPa*s.

2. The high-functionality polyisocyanate containing urethane groups according to claim 1, wherein the trialkanolamine (A) is at least one trialkanolamine selected from the group consisting of 5-[bis(2'-hydroxyethyl)amino]-3-oxapentan-1-ol, triethanolamine, tripropanolamine, N-ethyldiethanolamine, N-methyldiethanolamine, and N-butyldiethanolamine.

3. The high-functionality polyisocyanate containing urethane groups according to claim 2, wherein the trialkanolamine (A) comprises triethanolamine 4. The high-functionality polyisocyanate containing urethane groups according to claim 2, wherein, in addition to the compound (A), 10% to 70% of the total amount of hydroxyl groups employed come from a diol (A1) and/or polyol (A2).

5. A method of coating comprising applying a two-component coating composition comprising the high-functionality polyisocyanate containing urethane groups according to claim 1.

6. A two-component coating composition comprising
   at least one high-functionality polyisocyanate containing urethane groups according to claim 1,
   at least one compound having at least 2 groups that are reactive toward isocyanate groups,
   optionally solvents, pigment, additives and/or thickeners.

7. A process for preparing a polyurethane coating material, which comprises reacting a high-functionality polyisocyanate containing urethane groups according to any claim 1 with at least one binder which comprises isocyanate-reactive groups.

8. A process for preparing polyurethane coating materials, which comprises reacting a high-functionality polyisocyanate containing urethane groups according to any of claim 1 with at least one binder selected from the group consisting of polyacrylate polyols, polyester polyols, polyether polyols, polyurethane polyols, polyurea polyols, polyetherols, polycarbonates, polyesterpolyacrylate polyols, polyesterpolyurethane polyols, polyurethanepolyacrylate polyols, polyurethane-modified alkyd resins, fatty-acid-modified polyesterpolyurethane polyols, copolymers with allyl ethers, and copolymers and graft polymers from the groups of compounds stated.

9. A method of curing a polyuretheane coating material comprising adding the high-functionality polyisocyanate containing urethane groups according to of claim 1 as a curing agent.

10. A method of curing comprising adding the high-functionality polyisocyanate containing urethane groups according to claim 1 as a curing agent to a composition used in a process selected from the group consisting of refinish-coating, wood-coating or large-vehicle-coating.

11. A method of curing comprising adding the high-functionality polyisocyanate containing urethane groups according to claim 1 as a curing agent to a composition selected from the group consisting of a coating material, an adhesive and a sealant.

* * * * *